US011090850B2

(12) United States Patent
Mouthuy

(10) Patent No.: US 11,090,850 B2
(45) Date of Patent: Aug. 17, 2021

(54) ELECTROSPUN FILAMENTS

(71) Applicant: ISIS INNOVATION LIMITED, Oxford (GB)

(72) Inventor: Pierre-Alexis Mouthuy, Oxford (GB)

(73) Assignee: OXFORD UNIVERSITY INNOVATION LIMITED, Oxford (GB)

(*) Notice: Subject to any disclaimer, the term of this patent is extended or adjusted under 35 U.S.C. 154(b) by 241 days.

(21) Appl. No.: 15/023,172

(22) PCT Filed: Sep. 18, 2014

(86) PCT No.: PCT/GB2014/052834
§ 371 (c)(1),
(2) Date: Mar. 18, 2016

(87) PCT Pub. No.: WO2015/040399
PCT Pub. Date: Mar. 26, 2015

(65) Prior Publication Data
US 2016/0229104 A1 Aug. 11, 2016

(30) Foreign Application Priority Data

Sep. 18, 2013 (GB) ..................... 1316577

(51) Int. Cl.
D01D 7/00 (2006.01)
D02G 1/02 (2006.01)
(Continued)

(52) U.S. Cl.
CPC ............. B29C 48/05 (2019.02); A61L 27/20 (2013.01); D01D 5/003 (2013.01); D01D 5/0023 (2013.01);
(Continued)

(58) Field of Classification Search
CPC .... D01D 5/0007; D01D 5/0023; D01D 5/003; D01D 5/0038; D01D 5/0046;
(Continued)

(56) References Cited

U.S. PATENT DOCUMENTS 1,975,504 A 10/1934 Formhals
2,116,942 A * 5/1938 Formhals ............. D01D 5/0076
264/10
2,187,306 A * 1/1940 Formhals ............. D01D 5/0076
264/171.14
(Continued)

FOREIGN PATENT DOCUMENTS

CN 101113540 A 1/2008
CN 101514507 A 8/2009
(Continued)

OTHER PUBLICATIONS

Phyllis G. Tortora et al., Understanding Textiles, 1997; Prentice-Hall, Inc./Simon & Schuster/A Viacom Company, Fifth Edition, pp. 226 and 227. (Year: 1997).*
(Continued)

Primary Examiner — Leo B Tentoni
(74) Attorney, Agent, or Firm — Fay Sharpe LLP

(57) ABSTRACT

A method for producing a continuous filament from electrospun fibers includes providing a conducting collection surface that is an elongate three-dimensional surface. An attractive electric field gradient is formed between the collection surface and a source of electrically charged fibers. The collection surface is moved in a longitudinal direction relative to the source of electrically charged fibers. The fibers are collected on the collection surface so as to form a continuous filament.

10 Claims, 13 Drawing Sheets

(51) Int. Cl.
*B29C 48/05* (2019.01)
*D01D 5/00* (2006.01)
*D01D 5/16* (2006.01)
*A61L 27/20* (2006.01)
*B29L 31/00* (2006.01)

(52) U.S. Cl.
CPC ......... *D01D 5/0038* (2013.01); *D01D 5/0046* (2013.01); *D01D 5/0076* (2013.01); *D01D 5/16* (2013.01); *D02G 1/028* (2013.01); *A61L 2430/10* (2013.01); *B29L 2031/731* (2013.01); *D01D 5/0092* (2013.01)

(58) Field of Classification Search
CPC .. D01D 5/0076; D01D 7/00; B29L 2031/731; D02G 1/02; D02G 1/028
USPC .... 264/10, 103, 211.12, 438, 441, 464, 465, 264/466, 484; 57/1 R
See application file for complete search history.

(56) References Cited

U.S. PATENT DOCUMENTS

| | | | |
|---|---|---|---|
| 2008/0122142 A1 | 5/2008 | Kim et al. | |
| 2009/0324950 A1 | 12/2009 | Kim | |
| 2010/0222771 A1* | 9/2010 | Mitchell | D01D 5/0076 264/465 X |
| 2011/0247311 A1* | 10/2011 | Smit | D01D 5/0076 264/466 X |
| 2012/0295109 A1 | 11/2012 | Jirsak et al. | |
| 2014/0284827 A1* | 9/2014 | Pokorny | D01D 5/0076 264/6 |

FOREIGN PATENT DOCUMENTS

| | | |
|---|---|---|
| GB | 364780 | 1/1932 |
| GB | 2 494 277 A | 3/2013 |
| WO | WO 2005/073442 A1 | 8/2005 |
| WO | WO 2008/062264 A2 | 5/2008 |
| WO | WO 2009/049564 A2 | 4/2009 |

OTHER PUBLICATIONS

Ali et al., Electrospinning of Continuous Nanofiber Bundles and Twisted Nanofiber Yarns, Nanofibers—Production, Properties and Functional Applications, Dr. Tong Lin (Ed.), ISBN: 978-953-307-420-7, InTech, Chapter 8, pp. 153-174, Nov. 2011.

Smit et al., "Polymer Communication—Continuous Yarns From Electrospun Fibers", Polymer 46 (2005) pp. 2419-2423.

Teo et al., "Polymer Communication—A Dynamic Liquid Support System for Continuous Electrospun Yarn Fabrication", Polymer 48 (2007) pp. 3400-3405.

Theron et al., "Electrostatic Field-Assisted Alignment of Electrospun Nanofibres", Nanotechnology 12 (2001) pp. 384-390.

Yousefzadeh et al., "Producing Continuous Twisted Yarn From Well-Aligned Nanofibers by Water Vortex", Polymer Engineering and Science, 2011, pp. 323-329.

International Search Report and Written Opinion of International Application No. PCT/GB2014/052834 dated Nov. 24, 2014, 11 pages.

Search Report of British Application Serial No. 1316577.4 dated Mar. 7, 2014, 2 pages.

* cited by examiner

ELECTROSPUN FILAMENTS

BACKGROUND

The present invention relates to methods and apparatus for collecting electrically charged fibres, in particular electrospun fibres. The present invention may be used to fabricate continuous filaments made of electrospun fibres.

Electrospun fibres are typically formed by applying a high voltage to a polymer solution as it is discharged from a nozzle. The viscosity of the polymer solution prevents the liquid from breaking up into droplets due to surface tension and instead causes the liquid solution to remain as a jet that solidifies into fibres due to solvent evaporation. Electrospinning naturally produces nonwoven fibre mats if a planar stationary plate is used as a collector. These may be randomly-oriented nonwoven fibre mats, which result from the "whipping instability" of the electrospinning jet. Alternatively, some electrospinning techniques may produce meshes containing aligned, random or grid-like fibres by using different shaped collectors. However, very little work has been done to produce woven electrospun materials, which requires the electrospun fibres to be arranged in a particular way before they are able to be used.

There have been various proposals to manipulate the electric field, or use moving collector or spinneret systems, so as to collect fibre bundles rather than mats. Those bundles can be collected in a continuous or discontinuous way. Continuous bundles of electrospun fibres may be drawn from liquid collectors or collected using a dynamic mechanical collector, such as a cylindrical drum or tapered wheel. An example of the use of liquid collectors can be found in Teo et al (Polymer 48 (2007) 3400-3405). However, liquid collectors are inconvenient for a number of reasons. The bundles produced have only low levels of linking between fibres, causing variation in bundle diameter and bundle breakage due to the surface tension of the water. The nanofibre morphology can be affected by water vapour, and in addition water solubility affects the materials which may be used, both in the direct spinning of polymers and in the incorporation of drugs into fibres.

U.S. Pat. No. 1,975,504 describes a movable fibre collecting device consisting of a rotating wheel or an endless steel band. Electrospun fibres pile up on the collecting device as a random mat and can then be pushed together to form a bundle of fibres. Although such a dynamic collector may produce some aligned fibres, the result is merely a bundle of loosely assembled fibres which can easily come apart as there is little interaction between fibres to hold them together. Furthermore, many previous collection techniques lack robustness and reliability.

With nonwoven electrospun mats, the relatively low mechanical strength and difficulty in tailoring the fibrous structure have restricted their applications. With techniques that obtain bundles of fibres from an electrospinning process, the fibres so produced are often of limited length and thickness. Single electrospun fibres, especially nanofibres having a diameter less than 1 µm, are generally too thin and fragile to be wound into yarn or woven into fibrous structures. Other than forming bundles of fibres, some alternative processes twist groups of fibres into yarns as they are collected from an electrospinning process. Polymers including peroxyacyl nitrates (PAN), polycaprolactone (PCL) and phenol formaldehyde (PF) have been successfully electrospun directly into twisted continuous yarns using a rotary funnel collector and two oppositely charged spinnerets.

Compared to traditional materials for tissue repair applications, electrospun materials have been found to promote active wound healing. The dimensions of the fibres created by electrospinning can be similar to those found in the native extracellular matrix, and this feature can be used to improve tissue repair by promoting cell adhesion, proliferation and invasion. It has also been shown that the small diameter of electrospun fibres results in a decreased inflammatory response compared to scaffolds with larger fibre diameters or non-fibrous structures. Due to the small diameter of the fibres, they have many useful properties such as a high surface area to volume ratio, and high porosity. These make them very desirable as implantable materials. They can also be used for the introduction of active agents such as antibacterial or growth factors, as they can both carry and release these agents in a controlled manner. The present techniques for producing monofilaments or twisted yarns of fibres from some polymers of biomedical interest, for example polydioxonone (PDO), are of limited value due to inconsistencies in yarn diameter and twist number, with few links between fibres. These issues reduce their potential use as materials for tissue repair applications.

A potential problem with current monofilaments and twisted yarns is that they lack in surface features. Nanofibres produced from electrospinning naturally have a non-crystalline structure owing to the rapid solidification of the spinning jet. The high surface area and morphology of this porous structure can make them highly biocompatible, mimicking the fibrous matrix surrounding the cells in bodily tissues and organs. Structures made of electrospun fibres have therefore been investigated as scaffolds for tissue engineering. Nonwoven electrospun materials often lack mechanical strength, preventing their use in tissues that are exposed to large mechanical forces such as musculoskeletal tissues. In particular, aligned electrospun fibres have already shown their potential as scaffolds for tendon tissue engineering. However the fibres are typically drawn to cause alignment and annealed to improve crystalline structure and mechanical strength. Alternatively, nonwoven materials may need to be supported in order to increase their mechanical strength, for example by woven or braided structures or by thick monofibres.

There remains a need for robust and scalable techniques of manufacturing continuous filaments of electrospun fibres with adequate mechanical properties.

BRIEF SUMMARY

According to a first aspect of the present invention there is provided a method for producing a continuous filament from electrospun fibres, the method comprising: providing a conducting collection surface that is an elongate, three-dimensional surface; forming an attractive electric field gradient between the collection surface and a source of electrically charged fibres; moving the collection surface in a longitudinal direction relative to the source of electrically charged fibres; and collecting the fibres on the collection surface so as to form a continuous filament.

Such a method using a three-dimensional collection surface has advantageously been found to produce a continuous filament of electrospun fibres that is highly textured. The fibres tend to interlink as they are collected randomly on the surface and the remaining solvent evaporates. The fibres may not distribute homogeneously across the surface. Due to the three-dimensional shape of the surface, more interlinks can be formed, creating a filament which is not flat and therefore is much stronger. By retaining the surface features and inhomogeneous structure of the fibres, the electrospun filament is more bio-mimetic in comparison with monofilaments and yarns frequently used in medical textiles, resulting in improved cell attachment and cell growth. Furthermore the process is entirely scalable and easy to carry out.

A filament as produced by the present invention may be distinguished from a bundle or collection of electrospun fibres, as formed by prior art electrospinning techniques, by its mechanical integrity. Because the filament is not flat, the fibres tend to interlink in a three-dimensional structure. Interactions between the fibres in the three-dimensional network cause them to bond together in a way that is not possible in a random mat of collected fibres.

In a set of embodiments, the elongate three-dimensional surface is provided by a conducting wire. It is postulated that the three-dimensional collection surface, such as the surface of a wire with small diameter, may allow the electrospun fibres to interact and form cross-links which result in adherence not found in a bundled collection of separate electrospun fibres and therefore stronger mechanical properties than found in bundled collections. Moreover, these filaments have been found to be more pliable, flexible and softer than monofilaments, meaning that they do not suffer from the problem of shape memory as monofilaments do. These properties make the electrospun filaments more suitable for weaving, plaiting, etc.

The Applicant has surprisingly found that a continuous filament made of electrospun fibres may have more desirable properties when the fibres are randomly arranged during collection and the filament subsequently undergoes a stretching treatment so as to align the fibres along its axis. Accordingly the method may further comprise the step of subsequently stretching the continuous filament so as to align the fibres, preferably in a longitudinal direction. Stretching the filament has been found to improve the strength at break. The stretched filament may be stronger than electrospun bundles collected using other techniques, because the three-dimensional collection surface allows links to be formed between the polymer fibres as they are deposited and before they are aligned. It can be important to align the fibres along the axis of the filament for tissue engineering applications, as aligned electrospun fibres are known to cause the cells to elongate in the direction of the fibre alignment. This might be crucial for example in the case of tendon repair, because native tenocytes have a one-directional shape. The subsequent stretching step may increase the length of the filament to up to about 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390% or 400%. This stretching step may be assisted by conventional post-treatment methods, such as the placement of the filament in a hot bath during stretching.

The method may comprise the step of separating the continuous filament from the collection surface. Due to the shape of the collection surface, i.e. the small, three-dimensional surface that provides a relatively small surface area compared to the size of the filament on which the fibres can collect, the filament can be easily removed from the collection surface. This is because the fibres pile up predominantly on one side of the collection surface, e.g. facing the source, rather than being spread over a large surface area. Interactions between the fibres form a strong filament which does not break easily as it is removed from the collection surface. Preferably the continuous filament is separated from the collection surface before stretching the continuous filament so as to align the fibres, where this step is used. The filament may be separated from the collection surface after one or more optional treatment steps have been performed. For example, the filament may be coated with a material, such as a non-fibrous polymer layer, before being separated. Separation may be aided, for example, by using a cutting or abrasive tool, e.g. a blade, to separate the continuous filament from the collection surface. Alternatively, or in addition, the continuous filament may be separated from the collection surface using one or more of: laser; heat; solvent e.g. to effectively "melt" the filament on one side of the collection surface. Alternatively, or in addition, separation may comprise immersing the continuous filament in a liquid to separate it from the collection surface. For example, the collection surface may be moved so as to pass the filament into a solvent bath to assist separation. This may also act as a washing process, for example in order to remove any excess solvent (from the spinning process) from the resulting filament.

The method may comprise the step of picking up the continuous filament after it has been separated from the collection surface. A mechanical and/or electrostatic pickup technique may be used. The filament may be immediately post-processed, for example stretched, or subsequent treatment steps may be carried out at a later time and/or different location. The method may comprise collecting the continuous filament on a reel e.g. for storage and/or transportation before post-processing steps are applied.

It has been found that electrospun fibres tend to bond together in an improved way when deposited on an elongate, three-dimensional collection surface. However, it is possible that some fibres may not be wholly attracted to the collection surface and may bridge across to one or more other surfaces present nearby, including other surfaces of a collector that provides the collection surface. The Applicant has realised that it is desirable to prevent fibres spanning away from the continuous filament. In one set of embodiments, the method may therefore comprise moving the collection surface with or relative to a non-conducting (or less conductive) device spaced radially from the collection surface to interrupt trailing fibres. The non-conducting device may comprise a blade to cut any trailing fibres. The non-conducting device may comprise a guide, for example a guide with a lower conductivity or a lower electrical charge as compared to the collection surface, to direct fibres back towards the elongate collection surface. The guide may also be physically small, e.g. a metallic spike, in order to minimise the number of fibres which bridge to it. The device may be static, for example an annular device arranged circumferentially around the collection surface such that the collector moves relative to the device causing cutting/repulsion of fibres, or it may be dynamic, for example moving along with the collection surface at a suitable speed. It is beneficial to cut any trailing fibres as soon as possible if they begin to form bridges, in order to minimise weakening of the filament, and therefore a dynamic non-conducting (or less conductive) device is preferable. In addition, nearby surfaces can be treated such that they repel (or at least do not attract) the electrically charged fibres, in order to minimise bridging away from the collection surface.

Alternatively or additionally, a non-conductive (or less conductive) shield may be arranged adjacent to the collection surface, e.g. on an opposite side to the source, so as to prevent fibres collecting on surfaces other than the collection surface. This helps to decrease weakening of the fibre and increase ease of separation of the filament from the collection surface. The non-conductive shield may comprise an elongate surface which prevents fibres from bridging away from the collection surface. This shield may be static, allowing the collection surface to move along it, but in a set of embodiments it is dynamic and moves with the collection surface. Additionally or alternatively the non-conductive shield can be separated from the collection surface in order to help separate the filament. The shield may be charged such that it repels the electrospun fibres, potentially removing the need for a cutting or abrasive tool, as the number of fibres bridging will be minimal, and any that are present will be broken by separating the shield from the collection surface.

As the continuous filament is preferably separated from the collection surface at a point downstream of the source, the Applicant has recognised that the collection surface may conveniently be reused. Thus the method may comprise re-using the collection surface. In one set of embodiments the collection surface takes the form of an endless loop. This can be particularly easy to achieve in embodiments where the collection surface is the surface of an elongate wire. The collection surface may be cleaned before it is reused.

It will be appreciated that the amount of electrospun material deposited in the filament may be controlled by the speed at which the collection surface moves relative to the source. The method may therefore comprise selecting the speed at which the collection surface is moved. A dynamic collector may be arranged to move the three-dimensional collection surface at a varying speed, for example if it were desirable to form a filament having different density zones along its length. However, it may be preferable to form a filament having substantially the same density of electrospun fibres along its length, and thus in some embodiments the collection surface is moved at a substantially constant rate. Of course, the speed of the collection surface may be adjusted depending on factors such as the material of the electrospun fibres and various electrospinning parameters such as solution concentration, flow rate, desired filament diameter, spinning distance and/or applied voltage. The speed of the dynamic collector may be selected so as to be tailored to the particular fibres being collected. In one set of embodiments the method comprises moving the collection surface at a speed of between 2 and 20 cm per minute. Preferably the collection surface is moved at a speed of about 5-6 cm per minute in one set of embodiments. Preferably the collection surface is moved at a speed of about 3-4 cm per minute in another set of embodiments. Such relatively slow speeds may assist the collection surface in forming a continuous filament with entanglement or cross-links between the fibres. Higher speeds can be used in multi-nozzle setups, in which a plurality of nozzles are aligned with the collection surface and spin at least one type of fibre onto the collection surface. Nozzle-less setups could also be used. Multinozzle and nozzle-less setups can be used to increase speed of production of filaments formed from a single type of fibre, or alternatively to produce filaments formed from different types of fibre, e.g. intermingled or deposited in layers.

As is mentioned above, the method may be used to produce a filament made up a single type of electrospun fibre, or multiple types of fibre. Accordingly the method may comprise the step of collecting more than one different type of fibre on the collection surface. Different fibres may be deposited simultaneously or at different times, e.g. to build up a layered filament. The fibres may come from the same source or multiple sources. The different types of fibre may vary, for example, in terms of one or more of: chemical composition, diameter, length, etc and/or in terms of the electrospinning parameters used to generate the fibre e.g. choice of solvent, solution concentration, voltage, flow rate etc. This may be easier to achieve where the method comprises providing more than one source of electrically charged fibres.

Continuous filaments produced by this method are well-suited for making yarns and fabrics because their sub-microfibrous structure means that they are highly flexible and compliant, causing them to have less shape memory. In one set of embodiments the method further comprises twisting the continuous filament together with one or more other such filaments to produce a yarn. This may involve twisting filaments formed from the same fibres, but in a set of embodiments a plurality of different filament types are used to produce a mixed yarn. Preferably this twisting step is carried out after stretching of the filaments. As is mentioned above, stretching may be accompanied and/or followed by washing the filaments. The method may comprise twisting the multiple filaments in one or more directions, with a twist ratio such that the electrospun fibres in the final yarn are aligned along the axis of the yarn. Preferably the method comprises twisting together M filaments in a first direction to form a thread and then twisting together N threads in a second direction opposite to the first direction. In one example, $M=2N$. Such twisting results in a yarn having good mechanical strength as the fibres tend to be aligned along the axis of the yarn. If the filaments are twisted such that $M=N$, there is no residual tension in the yarn, meaning that it would not unwind if cut. The filaments may be produced separately. However the method may be optimised to produce yarns immediately by providing multiple collection surfaces in parallel to form multiple filaments. The multiple filaments may be formed simultaneously. Preferably the method comprises twisting the multiple filaments together to produce a yarn. The multiple filaments may be made from the same or different electrospun fibres.

The present invention extends to a filament made according to the methods described herein. Such a filament preferably has a diameter less than 1 mm, further preferably around 100 µm or less.

The present invention further extends to a yarn formed by twisting together two or more such filaments and/or a fabric formed by weaving together one or more strands or yarns of such filament(s). Electrospun yarns and fabrics are advantageous in comparison to nonwoven materials. For example, they have improved mechanical properties, for example flexibility and elasticity. In addition, the structure can be changed in order to alter further properties such as porosity and pore size, both in yarns and in a woven product. This may be assisted by the stretching process (where used), helping to prevent deformation of the filament, which might render the resulting yarn or fabric useless.

According to a second aspect of the present invention there is provided an apparatus for collecting electrospun fibres, comprising a dynamic collector having a conducting collection surface arranged to move relative to a source of electrically charged fibres whilst providing an attractive electric field gradient, wherein the collection surface is an elongate, three-dimensional surface moving in a longitudinal direction.

Such an apparatus having an elongate, three-dimensional collection surface has been found to form a continuous filament of electrospun fibres having beneficial properties, as already discussed above. It is beneficial that the apparatus does not involve a complicated set up or the use of liquid as a collector. This allows for easier incorporation of drugs into the filaments as they do not leach out into the liquid, and prevents other issues caused by liquid collectors such as bundle breakage and changes in fibre morphology, for example due to water vapour. Use of such apparatus has been found to offer very reproducible results and good control over the filament formation, for example enabling a user to control properties such as filament diameter, mechanical strength, length, etc.

It will be understood that the elongate collection surface defines a longitudinal direction in which it is much longer than it is wide. Because the three-dimensional collection surface is moving in this longitudinal direction, the fibres are forced to collect side by side and on top of one another in a three-dimensional heap, while extending continuously in the longitudinal direction. The way that the fibres pile up on the three-dimensional surface seems to allow linkages to naturally form between the fibres. It is postulated that chemical cross-links, hydrophobic forces and/or mechanical adherence may be involved. The three-dimensional surface may not be wholly continuous, for example the fibres may be able to span breaks in the surface in the longitudinal direction without disrupting the formation of a continuous filament. However, it is preferable that the three-dimensional surface is substantially continuous, at least in a circumferential direction, and optionally in the longitudinal direction.

The three-dimensional surface may have any suitable shape, including curved and angular shapes. It is envisaged that the three-dimensional collection surface may be formed by the interior walls of one or more elongate grooves formed in the dynamic collector, or the outer surfaces of one or more elongate ribs formed on the collector. However, it may not be easy to separate the continuous filament from the collection surface in such cases. In one set of embodiments, the elongate three-dimensional collection surface may be provided by a conducting wire. A wire may be used because it has a very high aspect ratio, i.e. its length in a longitudinal direction is much greater than its width or diameter. The wire may have a cross-section that is circular, oval, egg-shaped, diamond-shaped, triangular, rectangular, square, etc. Alternatively, a wire may have an 'N'-shaped cross-section or a U-shaped cross-section, such that any fibres bridging the gap between the legs can be easily cut, facilitating the separation of the filament from the collector. It is also preferable that the wire is strong enough and/or held under sufficient tension that it stays straight as it moves relative to the source. Preferably the dynamic collector consists of a substantially straight wire.

The diameter of the elongate three-dimensional collection surface e.g. wire may be chosen to form filaments of a desired size. It is an advantage of the present invention that the fibres entangle to form the filament as they are collected, rather than gathering up a substantially two-dimensional mat of fibres to produce a bundle. The collection surface preferably has a lateral extent e.g. diameter that is less than 1 mm. For example, the collection surface may be provided by a wire having a diameter of around 100 µm. In addition, or alternatively, the collection surface (e.g. a wire) may be positioned at a distance of about 10-20 cm from the source.

The conducting collection surface may be made from or coated by any suitable conducting material, for example graphite, but is preferably a metallic material. In one example the collection surface is formed of stainless steel, as this may make it easier to remove the filament from the surface after collection. It is surprising that a filament formed using the apparatus can be easily removed from the collection surface. In a set of embodiments, the collector is formed from a plurality of materials in order to minimise the bridging of fibres. For example, using a conducting material on the collection surface e.g. a side of the collector facing the source and a non-conducting material on another side of the collector such that the fibres are not attracted away from the collection surface. In a set of embodiments, the non-conducting material forms a shield as described above. The collector may be formed from two separate materials, or it may be a coating on at least one section of the collector's surface.

The dynamic collector may be arranged to move the three-dimensional collection surface at a substantially constant rate. Of course, the speed of the collection surface may be adjusted depending on factors such as the material of the electrospun fibres and various electrospinning parameters such as e.g. choice of solvent, solution concentration, flow rate, spinning distance and/or applied voltage. In one set of embodiments the collection surface may be moved at a speed of between 2 and 20 cm per minute. Preferably the collection surface is moved at a speed of about 3-4 or 5-6 cm per minute e.g. for a single pass below the source.

As is mentioned above, it is possible that some fibres may not be wholly attracted to the collection surface and may bridge across to another surface present close to the apparatus. The apparatus may therefore further comprise a non-conducting device arranged at a distance from the collection surface so as to help entrain any fibres trailing away from the longitudinal direction. The device may, for example, have a sharpened edge or abrasive surface that acts as a cutting blade. The device may be static, for example an annular device arranged circumferentially around the collection surface, or it may be dynamic, for example sweeping across the collection surface at a suitable distance.

In addition, or alternatively, the collection of fibres on the dynamic electrode may be augmented by providing one or more auxiliary electrodes in the vicinity of the collection surface. Such electrode(s) may be used, for example, to increase and/or shape the electric field experienced by the fibres so as to guide the deposition of fibres. In a set of embodiments, the shape of the electric field is such that the fibres are fully aligned and no stretching step is required to align them. An auxiliary electrode may therefore be arranged to encourage deposition of the fibres on the collection surface. The resulting electric field may help to attract fibres to the collection surface so that there are no trailing fibres.

As the filament is preferably separated from the collection surface at a point downstream, the Applicant has recognised that the collection surface may conveniently be re-used. The dynamic collector may be wound onto a reel and used again. In one set of embodiments the collection surface takes the form of an endless loop. This may be particularly straightforward to achieve when the collection surface is provided by a conducting wire. The collector, or at least the collection surface, may be cleaned before it is re-used.

The continuous filament may be separated from the collection surface by any suitable means, e.g. peeled away using mechanical force. Preferably the apparatus comprises means for assisting in separation of the continuous filament from the collection surface, such as a blade. A rotating wheel that carries one or more blades may be used to separate the filament as part of a continuous process. Alternatively, or in addition, the continuous filament may be immersed in a liquid to help separate it from the collection surface. For example, the collector may be used to move the filament into a solvent bath to assist separation.

After the filament has been separated from the collection surface, it may be picked up by any suitable means. In one set of examples, the filament may be picked up electrostatically. In another set of embodiments the filaments may be picked up mechanically. The filament may be immediately post-processed, for example stretched, or subsequent treatment steps may be carried out separately. The separated filament may therefore be collected on a reel or the like for storage and/or transportation before post-processing steps are applied.

As is described above, the continuous filament can be detached from the collection surface and optionally stretched to align the electrospun fibres. The stretched or unstretched filaments can be assembled into yarns by twisting or braiding multiple filaments together. The filaments or yarns may be knitted, woven or plaited into fabrics which are particularly well suited for medical applications such as orthopaedic or soft tissue repair, particularly in sutures, implants and tissue scaffolds. Woven electrospun structures may have potential for the repair of tendon tears, for example during shoulder surgeries. As mentioned previously, chemicals may be incorporated into the fibres, allowing for the implantation of bioactive agents such as vitamins, growth factors or antibacterial nanoparticles.

Of course filaments, yarns and fabrics made according to embodiments of the present invention may find use in a wide range of applications in non-medical fields such as filtration, protective materials, electrical and optical applications, sensors, environmental engineering (e.g. repair of gas/water filters), smart materials etc.

Embodiments of the present invention can be used to form filaments from the electrically charged fibres produced by any electrospinning source, including nozzles and nozzle-less techniques. Preferably it is a continuous source of electrically charged fibres. According to an embodiment of the present invention there is provided an electrospinning apparatus comprising a source of electrically charged fibres and a dynamic collector as described above. The distance between the electrospinning source and the dynamic collector is not critical. However it is convenient for the distance to be less than 50 cm so that the electrically charged fibres are attracted to the collector rather than elsewhere. This can also help to keep the apparatus compact for bench top use.

The electrospinning apparatus may comprise a conventional bench top electospinning device such as is commercially available from companies including Electrospinz, Fluence, KES Kato Tech Co., MECC, Nanospinner, NanoNC, Yflow, IME Technologies, Physics Instruments Co. and Linari Biomedical. The dynamic collector may simply be arranged within range of the usual discharge nozzle of the device. Where the electrospinning device has a discharge nozzle it may be easier to collect multiple different fibres, for example a multi-nozzle setup may be used. In one set of embodiments the apparatus may comprise a plurality of discharge nozzles aligned with the collection surface so as to spin fibres from more than one source. This setup can be used to increase the speed of filament production and/or to produce a filament formed from different types of fibre. However the collector is also compatible with nozzle-less electrospinning systems e.g. as offered by Elmarco in which a rotating drum is dipped into a bath of liquid polymer (so-called "nanospider" technology).

The electrospinning source may use an electrospinning liquid such as water, a liquid solution (aqueous solution, alcohol solution, organic solvent etc.), a particulate suspension in liquid, or even a liquid or molten polymer. Preferably the electrospinning liquid is a polymer solution, sol-gel, particulate suspension or melt. A polymer solution may include one or more polymers, one or more solvents, and optionally one or more cross-linking compounds. Polymers suitable for forming an electrospinning liquid include, for example, polyamides, polyimides, polyesters, polyacrylates, polysulfones, polycarbamides, polyolefins, polyurethanes, fluoropolymers, collagen, cellulose and cellulose acetate. Polymer mixtures, blends, copolymers and terpolymers may be used. Any suitable solvent may be used, either organic or inorganic. The solvent may be water, or an aqueous solution of a water-miscible solvent such as acetic acid, hydrochloric acid, acetone, tetrahydrofuran, ethanol or another alcohol.

For applications such as tissue repair, the fibres are preferably spun from a liquid polymer that is biologically compatible. In one example, the electrospun fibres are preferably formed from polydioxanone (PDO) or polycaprolactone (PCL). Examples of other suitable polymers include, but are not limited to, linear polyethylenimine, cellulose acetate, and other preferably grafted cellulosics, poly(L-lactic acid), polyethyleneoxide, and polyvinylpyrrolidone. A non-degradable polymer may be used, e.g. poly(ethylene terephthalate) (PET). Where the electrospun fibres are intended for wound healing applications, the liquid may comprise: a water-soluble polymer solution of poly(ethylene glycol) (PEG), poly(vinyl alcohol) (PVA), or poly(vinyl pyrrolidone) (PVP); or a non-water soluble polymer solution of biodegradable polyesters such as poly(lactic add) (PLLA), poly(lactic-co-glycolic add) (PLGA), polydioxanone (PDO), polyglycolic add (PGA), polyhydroxybutyrate (PHB) or polycaprolactone (PCL). Preferably the electrospun fibres are formed from a polymer solution comprising a solvent which is compatible with the skin or other tissue to be treated. Examples of such solvents include water, alcohols such as HFIP, and acetone. Active biological agents can also be incorporated into the electrospun fibres, for example vitamins, growth factors or antibacterial nanoparticles.

The electrospun fibres that are collected according to embodiments of the present invention are preferably nanofibres that are 1 µm or less in diameter. However fibres up to 10 µm may also be collected. Accordingly the fibres may have a diameter of at least 1 nm and up to 10 µm. Preferably the electrospun fibres are nanofibres having a diameter between 1 nm and 1000 nm, preferably between 10 nm and 1000 nm or between 100 nm and 1000 nm.

In the discussion above, it will be understood than an attractive electric field gradient may be created by the collection surface being charged differently from the electrically charged fibres. If, for example, the fibres are positively charged then the collection surface may be less positively charged, grounded or negatively charged. If, for example, the fibres are negatively charged then the collection surface may be less negatively charged, grounded or positively charged. In most cases a negative field gradient is preferably used, i.e. the collection surface being less charged than the fibres.

BRIEF DESCRIPTION OF THE DRAWINGS

Some preferred embodiments of the present invention will now be described, by way of example only, and with reference to the accompanying drawings, in which:

FIG. 10b shows how fibres build up on a collector using the setup of FIG. 10a;

DETAILED DESCRIPTION

Figure 1:
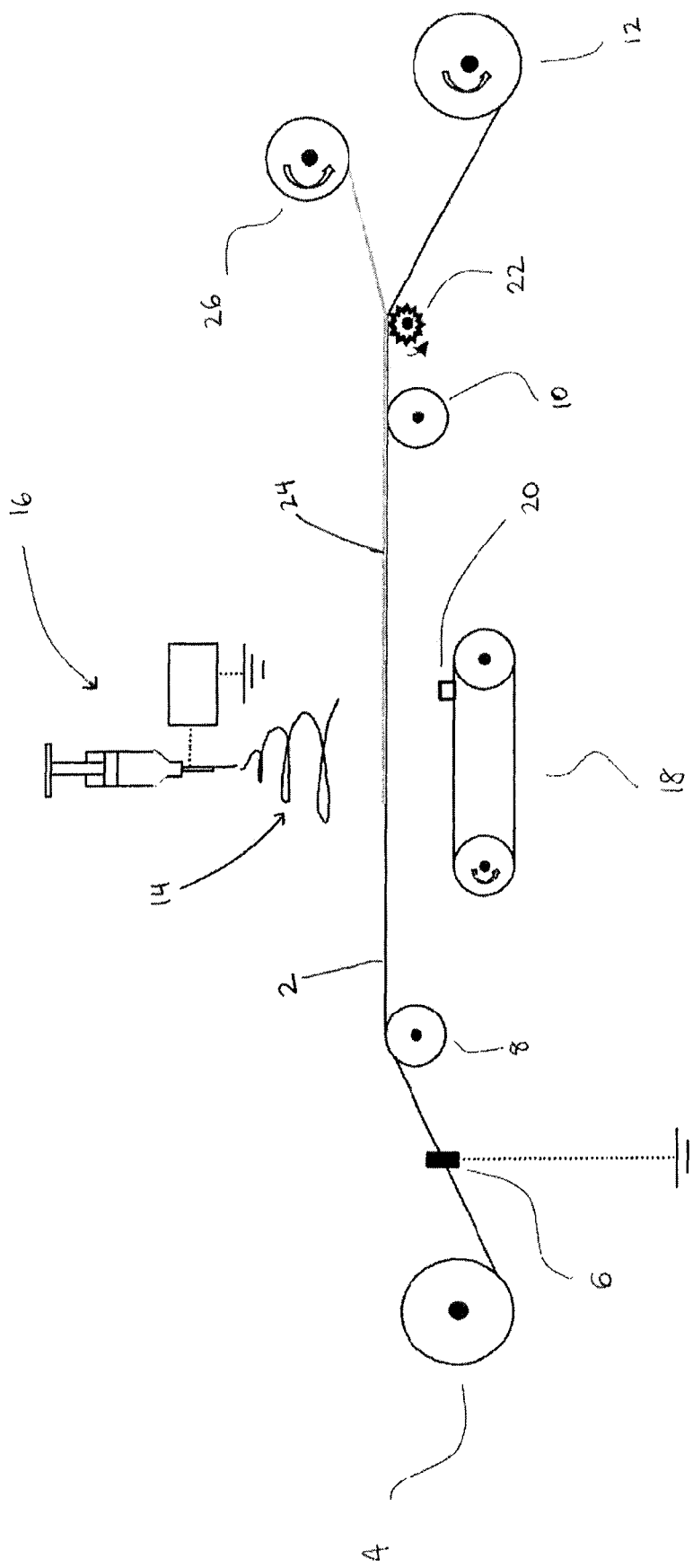
FIG. 1 shows a schematic of a collection apparatus according to a first embodiment.

FIG. 1 shows a schematic of apparatus which can be used to produce continuous filaments by collecting electrically charged fibres from an electrospinning device 16. A collection surface 2 is provided by a wire drawn from a wheel 4 through a brush contact 6 to ground. The wire 2 passes across two supporting wheels 8, 10, before being wound around a collecting wheel 12. As the straight wire 2 passes between the two supporting wheels 8, 10, electrically charged fibres 14 are deposited on the wire 2 from the electrospinning device 16, set at 8.6 kV. A sweeping system 18 is positioned below the wire 2, which is formed from a blade 20 circulating around two wheels. The blade 20 is formed from insulating material, and sweeps in a loop cutting any fibres 14 which are not fully attracted to the collecting wire 2 in order to prevent them 'bridging' to nearby surfaces. After the second supporting wheel 10, there is a filament separator 22. This is a notched wheel with blades in the notches, which is used to cut any fibres 14 which bridge underneath the wire 2, causing the filament 24 to be bound to the wire 2. The filament 24 can then be lifted off the wire 2 and wound onto a separate collecting wheel 26.

In use, the wire 2 is drawn underneath the fibre source 16 at 6 cm/min at a distance of about 20 cm from the source 16. The speed of the wire 2 is chosen in order to allow for fibres to be attracted to and collect onto its surface to a sufficient thickness that a three-dimensional filament 24 is produced. Due to the charged nature of the fibres 14, they may not all be attracted directly to the wire 2, and some may 'bridge' from the wire 2 to surrounding surfaces, or round the underside of the wire 2. These 'bridging' fibres are cut, either by the sweeper 18 or the filament separator 22, in order to prevent them causing weak points or breakages in the filament 24 and preventing correct deposition of subsequent fibres. The filament 24 which is formed can then be lifted from the collecting wire 2, either manually or automatically, and can be wound onto a collecting wheel 26. It can therefore be collected continuously, and cut to a desired length when the user decides. The collection wire 2 can also be collected after separation, and wound onto a separate wheel 12 for washing before it is re-used. Alternatively, the wire 2 could be looped back between wheels 8 and 10, such that it forms a continuous loop. The length of wire 2 between the two supporting wheels 8, 10 is sufficiently large that the wire 2 appears continuous to the fibres 14, and there are no end effects.

Figure 2:
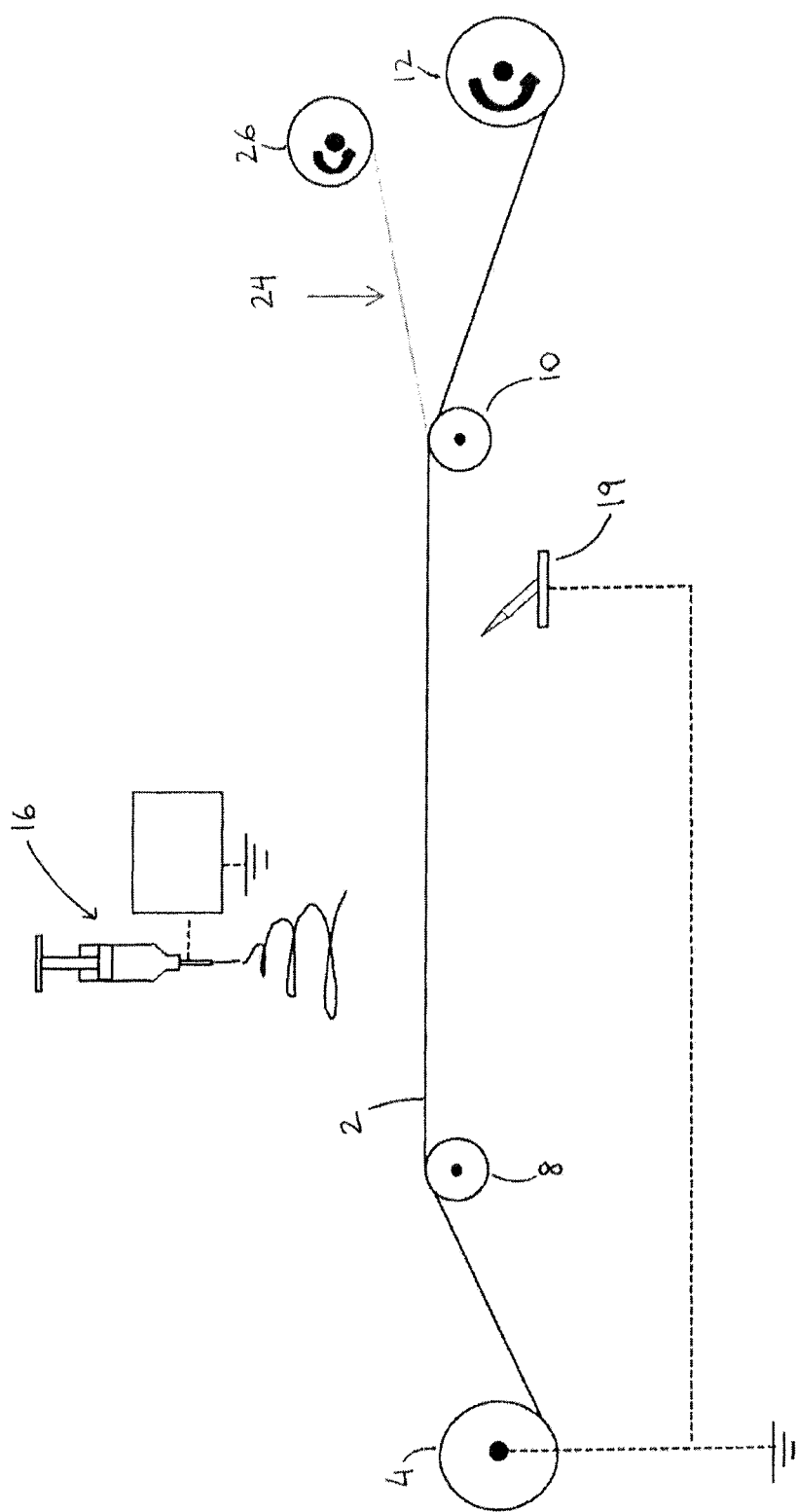
FIG. 2 shows a schematic of a collection apparatus according to a second embodiment.

FIG. 2 shows a schematic of an alternative apparatus, in which the sweeping system 18 is replaced by an auxiliary electrode 19. This electrode 19 generates an auxiliary electric field, encouraging the electrically charged fibres 14 to collect on the wire 2. The potential difference generated between the electrode 19 and the wire 2 helps to attract the fibres 14 to the collector. This helps prevent any fibres 14 'bridging' between the wire 2 and other surfaces, removing the need for a sweeping device 18 as in the previous embodiment.

Figure 3B:
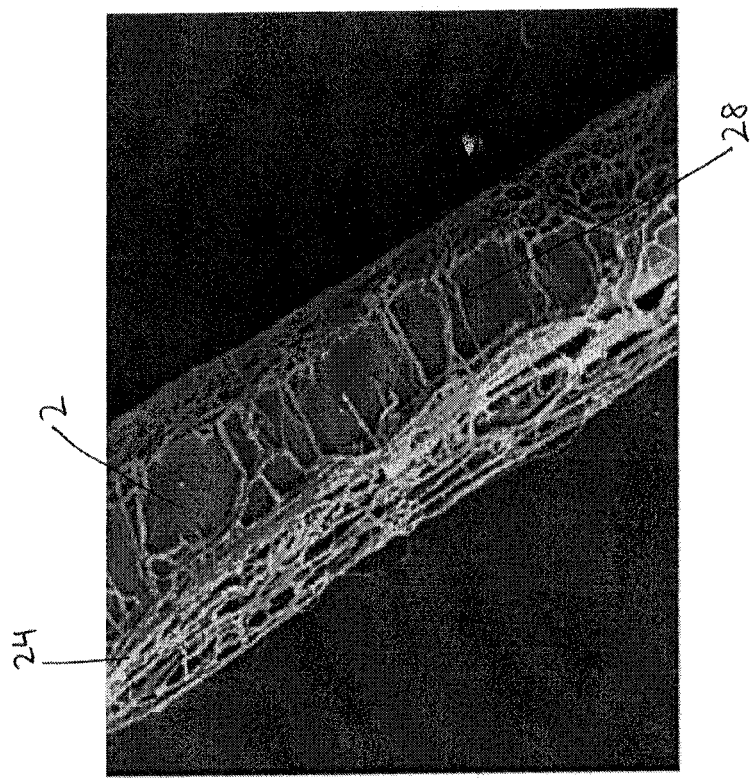
FIG. 3b shows the bottom of a filament on the collector of FIG. 1.
Figure 3A:
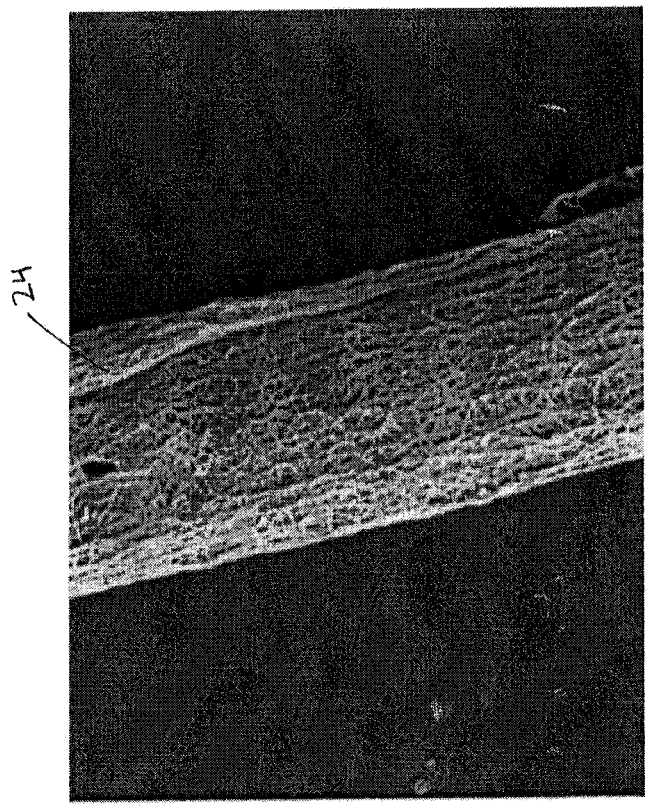
FIG. 3a shows the top of a filament on the collector of FIG. 1.

FIG. 3 shows a filament 24 as produced by the above apparatus, with FIG. 3a showing a top view of the filament 24, i.e. looking down from the spinning apparatus 16, and FIG. 3b showing a bottom view. While the majority of the fibres 14 collect on the three-dimensional upper surface of the wire 2, a number of fibres 28 bridge across and can be seen on the underneath of the wire 2, as in FIG. 3b. These bridging fibres 28 may weaken the structure of the filament 24, and are therefore cut by the separator 22 in order to prevent this weakening.

Figure 4B:
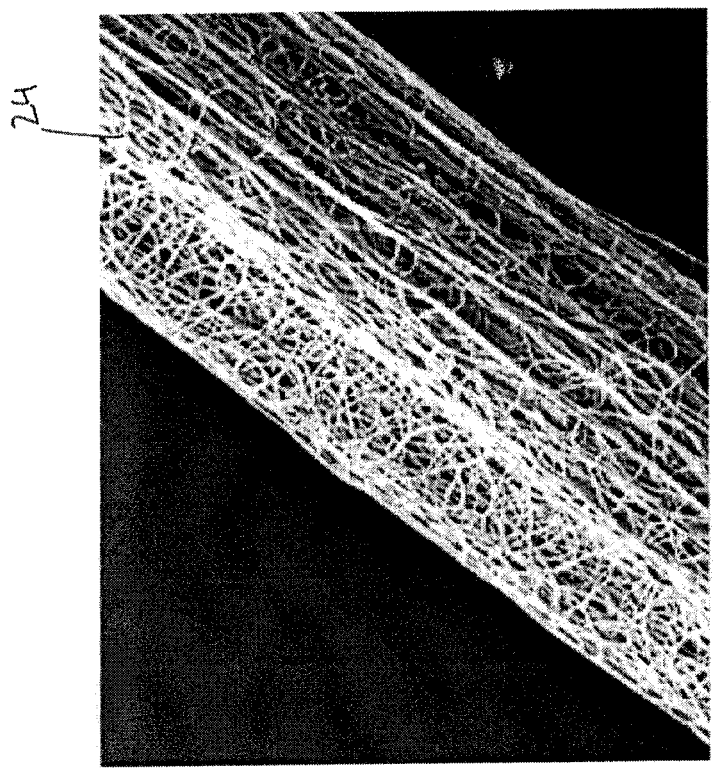
FIG. 4b shows the resulting filament.
Figure 4A:
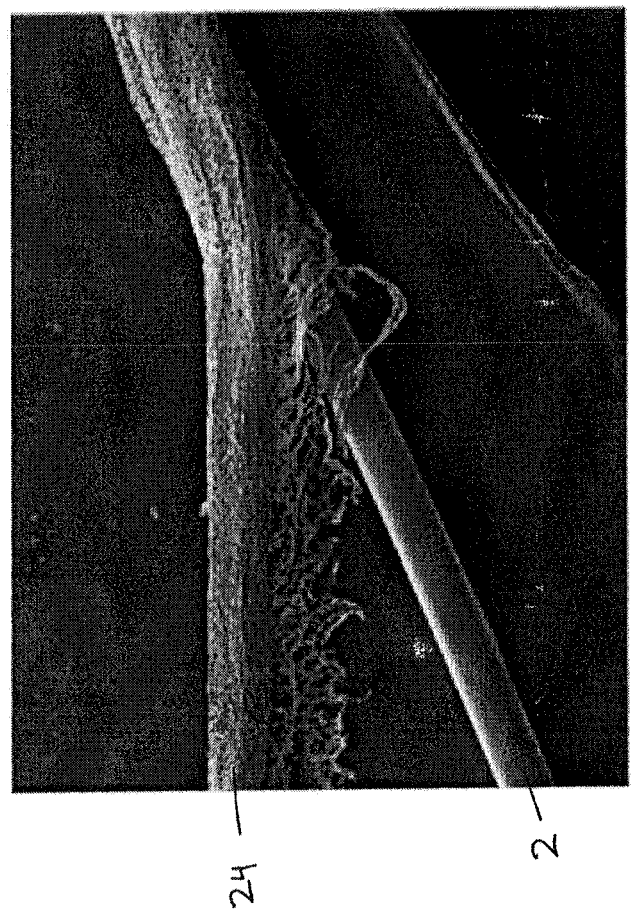
FIG. 4a shows the removal of a filament from the collector.
Figure 4C:
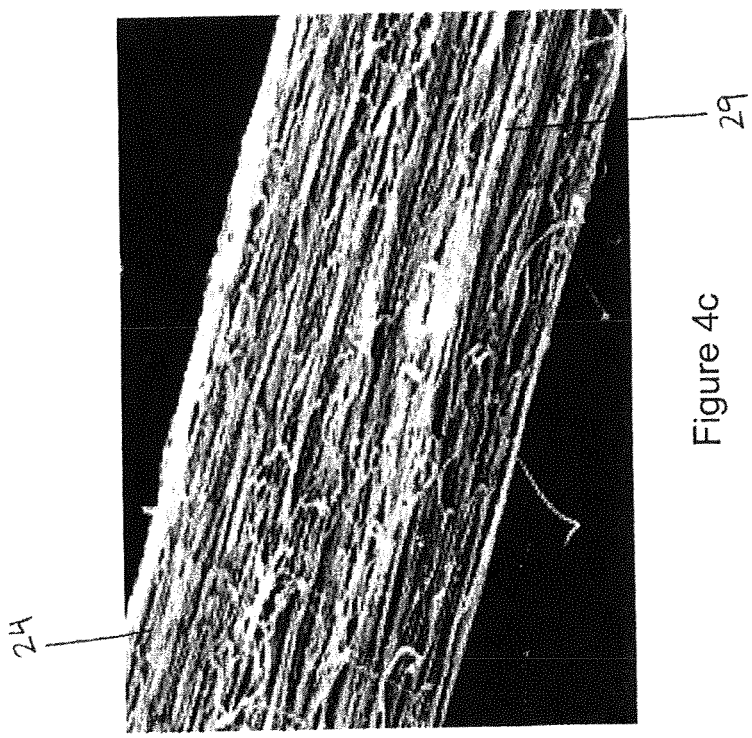
FIG. 4c shows the filament after subsequent stretching.

FIG. 4a shows a filament 24 as it is being separated from the collecting wire 2. This happens after the collector 2 passes over the separator 22, as any bridging fibres 28 are then cut and the filament 24 is released. The filament 24 is lifted from the collector 2, before being wound onto a collecting wheel 26. FIG. 4b shows a filament 24 which has been separated from the collecting wire 2. The fibres predominantly have random orientations. FIG. 4c shows a filament 24 after it has been stretched from 100 to 350%. In this example, the filament 24 has been stretched by 250% of its initial length. This stretching process has caused the fibres 29 to become aligned along the longitudinal axis of the filament 24. However, a large number of cross-links are still retained between the aligned fibres 29, increasing the strength of the filament 24 produced. The aligned fibres 29 are therefore connected to each other, rather than simply running adjacent to each other. This increases the strength of the resulting filament 24. The stretched filament 24 can then be used to make fabrics, either in this form or twisted together with other filaments to make a yarn.

FIGS. 4a to 4c demonstrate that using a wire as collector is an efficient method to concentrate the electrical field and assemble fibres as a dense, elongated mesh. This mesh can be detached into a filament without using a liquid such as ethanol to separate it from the wire. This offers a clear advantage particularly when incorporating bioactive molecules or when water-soluble polymers are used. The technology is simple, affordable and the use of motorised wheels offers excellent control over filament formation, detachment and collection.

Figure 5:
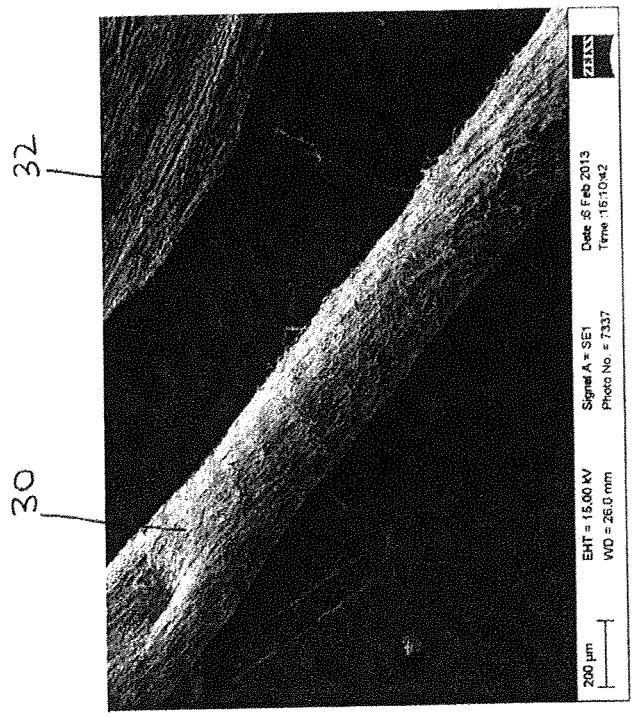
FIG. 5 shows a yarn as produced using prior art methods.

FIG. 5 shows a yarn 30 produced by prior art methods. Electrically charged fibres (generated at 7.3 kV) are collected on a grounded rotating drum, rotating at 2000 rpm at a distance of 20 cm from the source of the fibres, such that they produce a mesh 32. This mesh 32 is then lifted from the belt and rolled to produce a yarn 30. While this yarn may have a similar overall appearance, as it has been formed from rolling a flat mesh 32 there are no connections between the layers, making a weaker yarn than one produced by twisting filaments produced according to the present invention.

Figure 6:
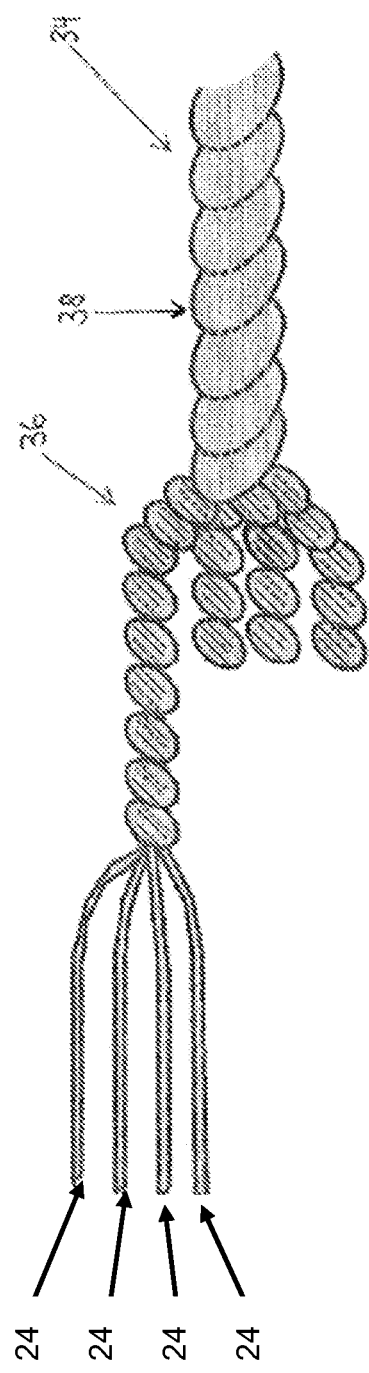
FIG. 6 shows a method of producing a spun yarn from a filament formed according to an embodiment of the present invention.

FIG. 6 demonstrates the method by which a yarn 34 can be produced from the electrospun filaments 24. In this example, a group of 16 filaments 24 are used to produce a yarn 34. The filaments 24 are twisted in groups of four in a right direction at 400 twists/m to form 'S' twists 36, before four groups of 'S' twists 36 are twisted together at 200 twists/m in a left direction to make 'Z' twists 38, and thereby produce a yarn 34. This ratio of 'S' twists 36 to 'Z' twists 38 (=2) has an additional benefit in that it results in the electrospun fibres being aligned along the axis of the yarn 34. Assembling filaments 24 into yarns 34 may be used to mimic the hierarchical structure of native tendon fascicles. The yarn 34 may be heat treated to activate an adhesive layer which can be electrospun onto the filaments 24, in order to hold the twists 36, 38 together. Of course other twisting patterns may be used.

Figure 7:
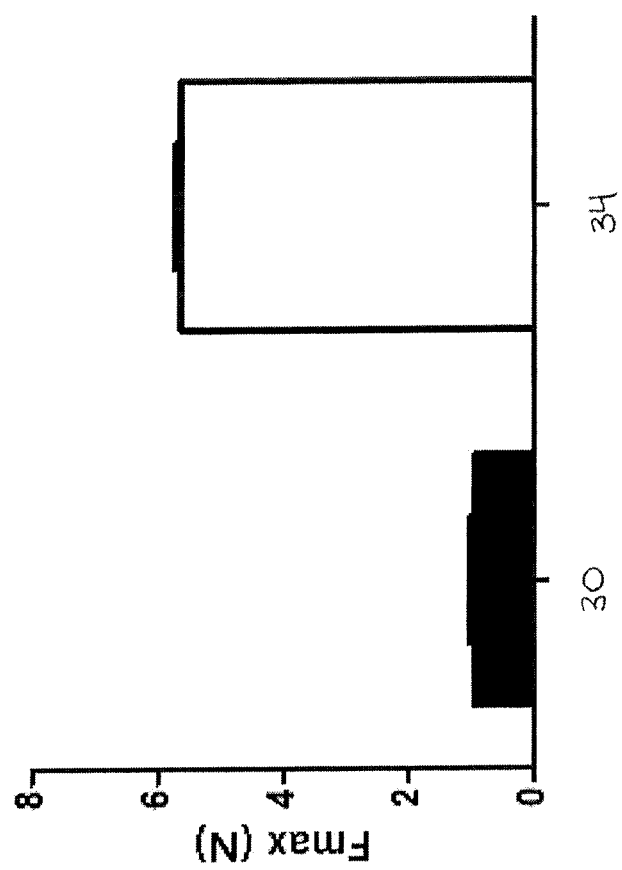
FIG. 7 is a graph comparing maximum force for yarns produced by prior art methods and those described herein.
Figure 8:
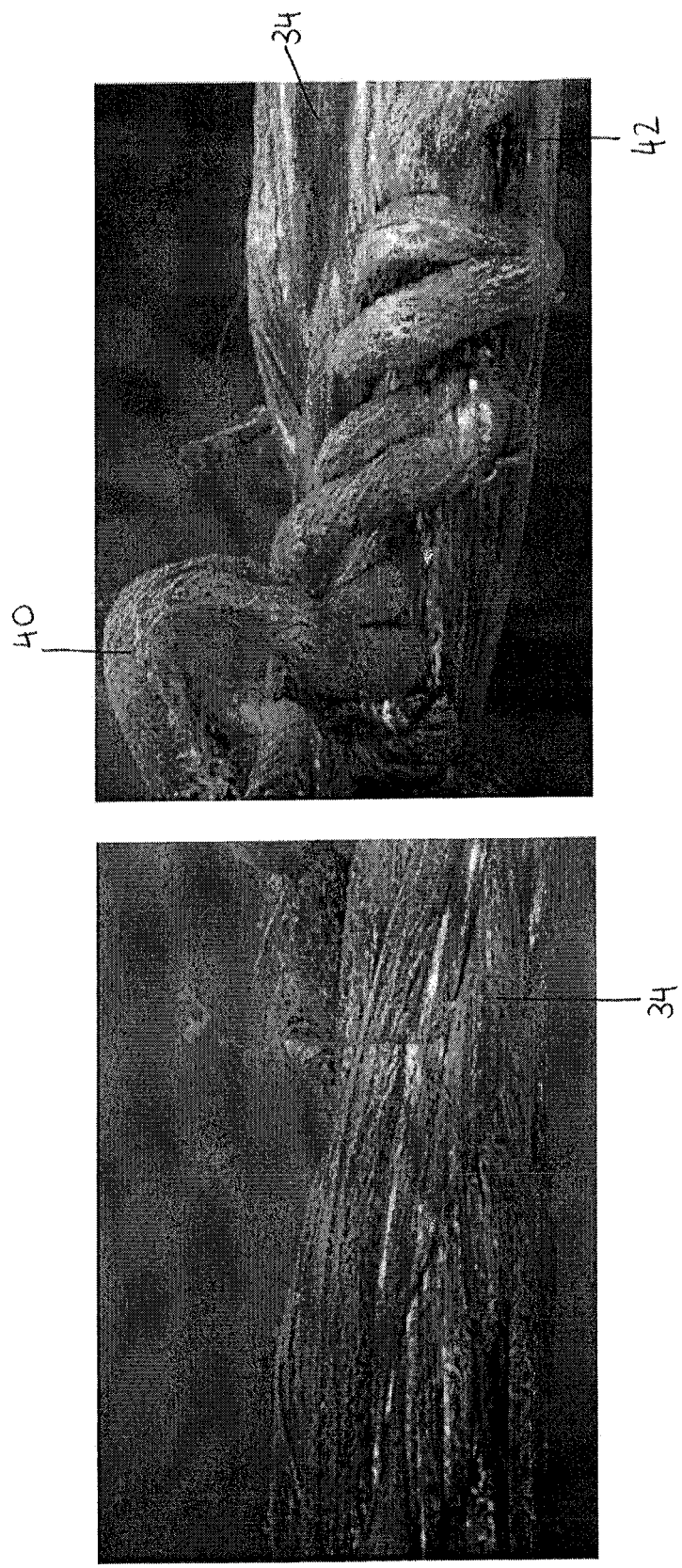
FIG. 8 shows a yarn produced by methods described herein as it is breaking.

The graph in FIG. 7 compares a rolled yarn 30, as demonstrated in FIG. 5, with a multifilament yarn 34, produced as in FIG. 6. Both yarns have roughly the same diameter, of between 300 and 400 µm, and were made of fibres spun from a solution of 9% polydioxanone (PDO) dissolved into 1,1,1,3,3,3-hexafluoroisopropanol (HFIP). As can be seen from the graph, the yarn 34 made of twisted filaments 24 can withstand more than five times as much force before breaking. In addition, due to the shape of the yarn 34, when it does begin to break, one broken filament 40 does not mean that the whole yarn 34 will break. This can be seen by FIG. 8, which demonstrates a yarn 34 as it is breaking. It is possible for one filament 40 to break while the other fifteen filaments 42 remain intact. For a rolled yarn 30, as the whole thing is produced from one electrospun mesh 32, when it begins to break it is liable for the entire yarn 30 to break.

Figure 9:
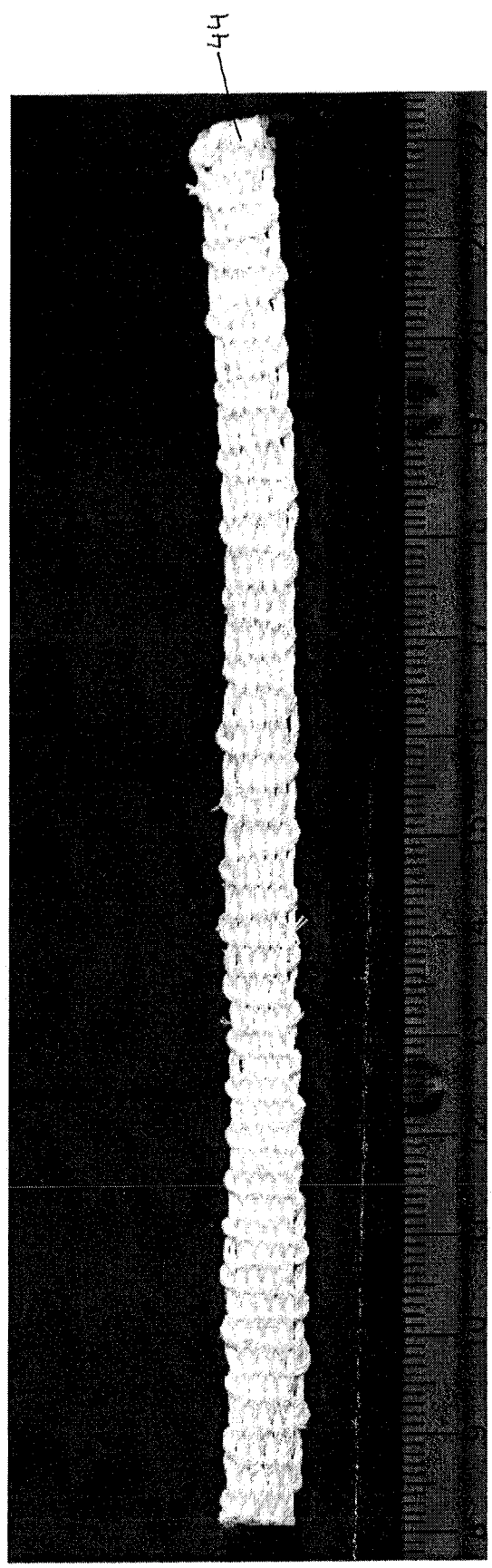
FIG. 9 shows a patch woven from filaments produced in accordance with an embodiment of the invention.

FIG. 9 shows a patch 44 produced from filaments 24 according to the invention. These filaments 24 have been twisted together to form a yarn 34, as in FIG. 6, before multiple yarns 34 have been woven to produce a fabric patch 44. This plain woven patch 44 can be used in medical applications, for example in orthopaedic repair. Cells can be cultured on the woven patches 44, as the multifibre filaments 24 have a texture which is more bio-mimetic and has improved cell attachment and growth in comparison with monofilaments.

Figure 10B:
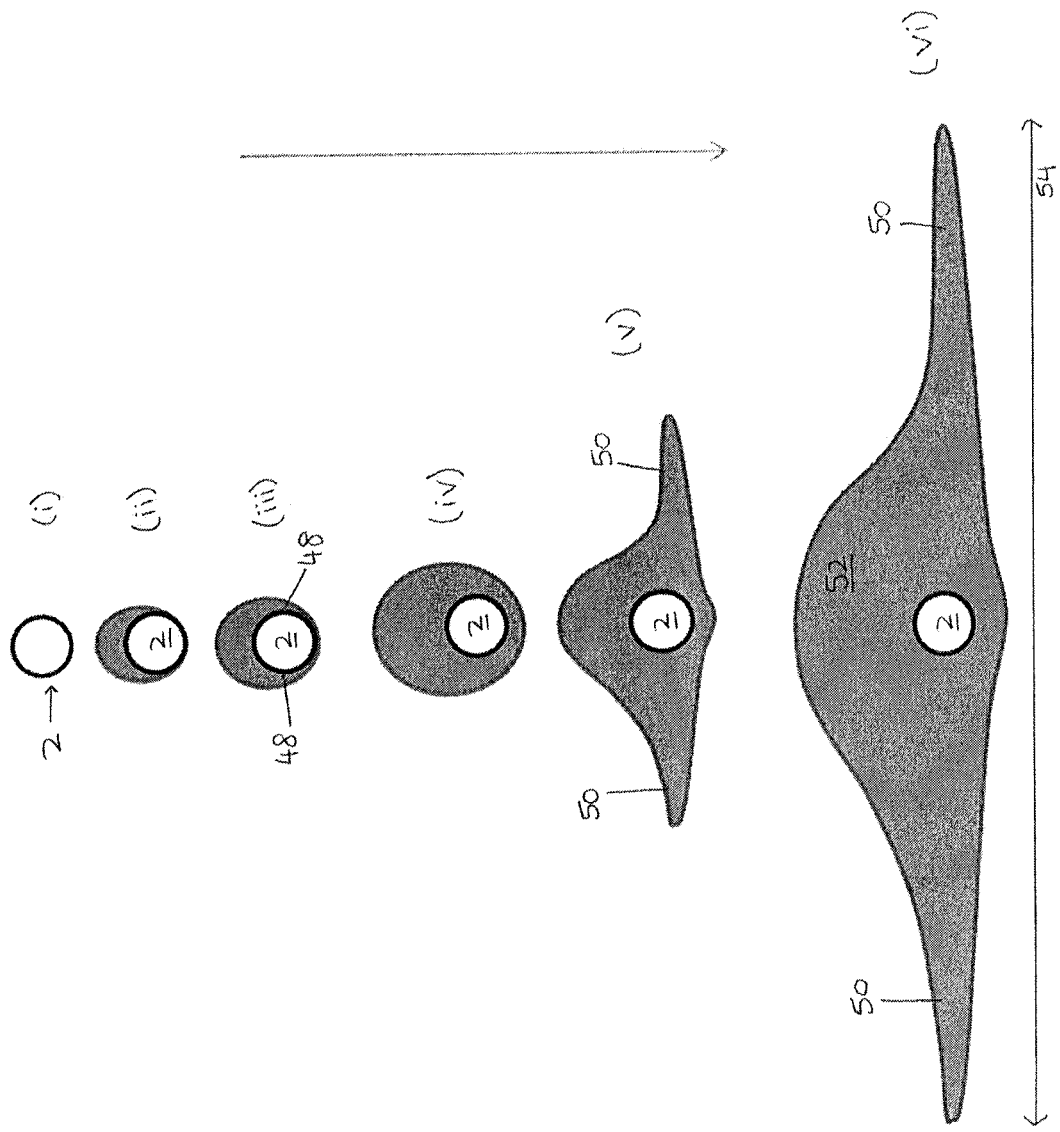
Figure 10A:
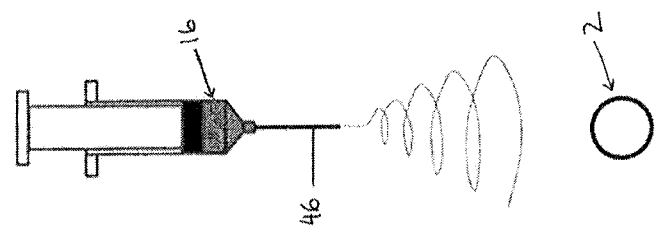
FIG. 10a shows a schematic of a spinning apparatus using a collection surface in accordance with the invention.

FIG. 10a shows a schematic of a spinning apparatus 16 with a collector according to the invention, in which the spinning apparatus 16 uses a nozzle 46 to spin fibres onto a collection wire 2. FIG. 10b demonstrates how the fibres spun from the nozzle 46 are collected on the wire 2. The six drawings (labelled (i) to (vi)) in FIG. 10b show how the fibres build up on the wire 2 with increased collection time. The collection time is increased by decreasing the speed at which the collection surface is drawn underneath the source or by increasing the rate at which fibres are deposited. The fibres predominantly collect on the collection surface, i.e. the side closest to the nozzle 46. However, as the wire 2 has a circular cross section, and is entirely formed from conducting material, the fibres spread around the wire 2 and relatively small numbers of fibres collect around the sides 48 causing a three-dimensional filament to be formed (see FIGS. 10b(ii) to 10b(iv)).

As increasingly large numbers of fibres collect on the wire 2, the filament begins to spread, forming wings 50 (see FIGS. 10b(v) and 10b(vi)). This is due to the fibres which are attached to the wire 2 forming an insulating layer around the wire 2, reducing the attractive force between the fibres and the wire 2. The fibres therefore do not attract as strongly to the wire 2, so do not conform as closely to the shape of the wire, causing the wings 50 to extend outwards. As can be seen from FIG. 10b(vi), while the filament 52 may eventually reach a size where it has a width 54 that is significantly larger than the diameter of the wire 2, it will still have a substantially three-dimensional shape due to the fibres predominantly collecting on side of the wire 2 near the nozzle 46.

The cross-sectional shape demonstrated is one example of how fibres may collect to form a filament. The shape of the filament may be determined by the materials used, both to form the electrospun fibres and the collector, as it is the attraction of the fibres to the collection surface which will determine the position of the fibres. The materials may be selected in order to achieve a desired filament cross-section, for example by having certain sections of the collector made from conducting material and others from non-conductive material, as discussed earlier.

EXAMPLE

Collecting Electrospun Fibres with a Grounded Wire, Fabricating Filaments and Assembling Filaments into Yarns An exemplary method used a thin conductive wire guide to collect electrospun fibres and form filaments. In the experimental setup, the wire 2 was placed underneath a electrospinning nozzle 16 as sketched in FIG. 1. The electrospinning solution was prepared by dissolving polydioxanone (PDO, viscosity 1.5-2.2 dl/g, Sigma-Aldrich Chemical Company Ltd., Dorset, UK) into 1,1,1,3,3,3-hexafluoroisopropanol (HFIP, Apollo Scientific Ltd., Cheshire, UK) at a concentration of 9% (weight to volume ratio).

The process consisted in electrospinning PDO fibres on a stainless steel wire (diameter 100 µm). The wire 2 was stretched between a feed wheel 4 and a motorised collection wheel 12 and was displaced at a rate of 3.7 cm/min. The distance between the nozzle 16 and the wire 2 was 20 cm and the average voltage applied was 8.6 kV. Underneath the wire 2, in the electrospinning region, a wiper (e.g. blade 20) was passing regularly to prevent fibres bridging from the wire 2. The distance between the wire 2 and the wiper 20 was set between 1 and 4 cm. The electrospun filament 24 was then continuously separated from the wire 2 further down the line and directly wound onto a second motorised collection wheel 26 rotating at the same speed as the wire collection wheel 12. Separation was facilitated by a wheel 22 with cutting teeth rotating at 500 rpm underneath the wire 2. The apparatus could be paused to refill the syringe with polymer solution and resumed without causing the filament 24 to break.

Figure 11B:
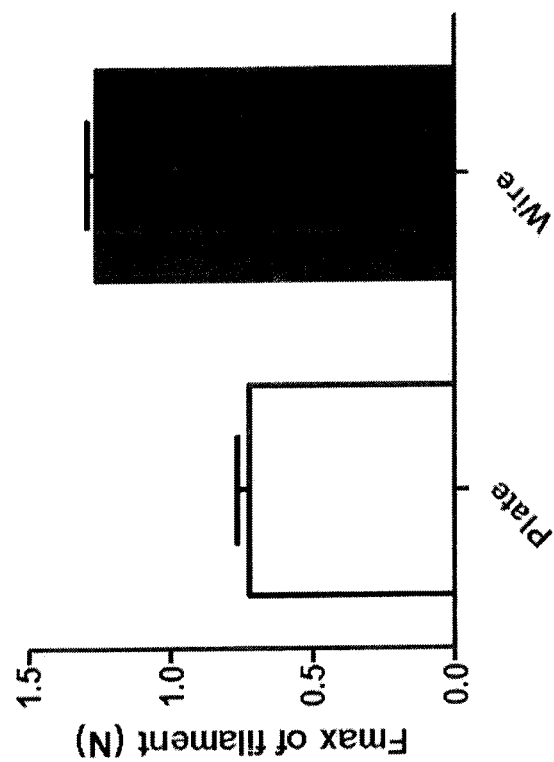
FIGS. 11a and 11b show how strength and strain is improved for filaments produced in accordance with an embodiment of the invention as compared to a flat mesh from a plate collector.
Figure 11A:
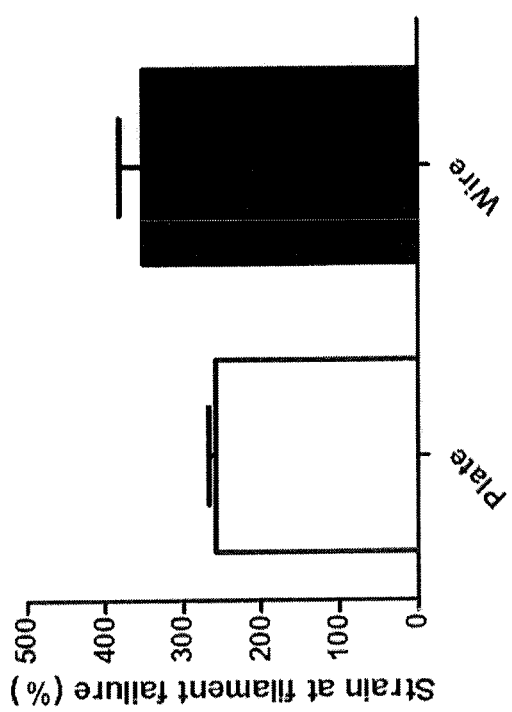

In this example, the polydioxanone (PDO) fibres were sprayed onto a grounded stainless steel wire. FIGS. 3a and 3b show SEM images of a filament 24 collected on a stainless steel wire 2 after electrospinning. It can be seen that the electrospun fibres deposited mostly on the side of the wire 2 exposed to the nozzle 16 compared to the hidden side. FIGS. 11a and 11b show the strength (Fmax) and failure strain measured for such a filament collected on a 100 µm wire, as compared to a filament formed from fibres collected on a flat plate. To fabricate filaments using a flat collector, a 10 cm wide aluminium band was stretched underneath the electrospinning nozzle 16 (distance of 20 cm) and was displaced at a rate of 3.7 cm/min. The average voltage applied was 8.6 kV. Meshes were then sprayed with ethanol 70% and rolled from one edge of the band to the other to produce filaments or test purposes. For tensile tests, specimens measuring 50 mm in length were tested to failure in tension using a Zwick machine at rate of 0.5 mm/min until failure.

Figure 12A:
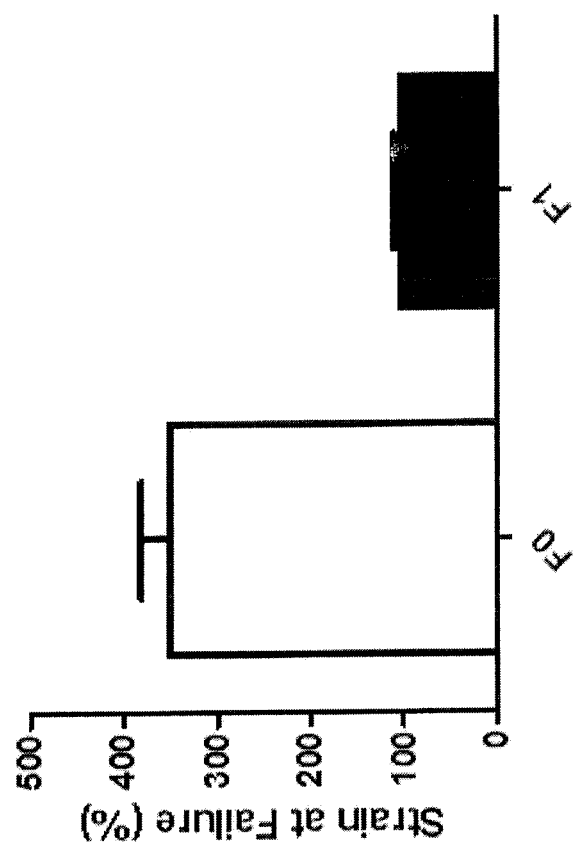
FIGS. 12a and 12b show how drawing (stretching) increases the force at break and reduces the strain.
Figure 12B:
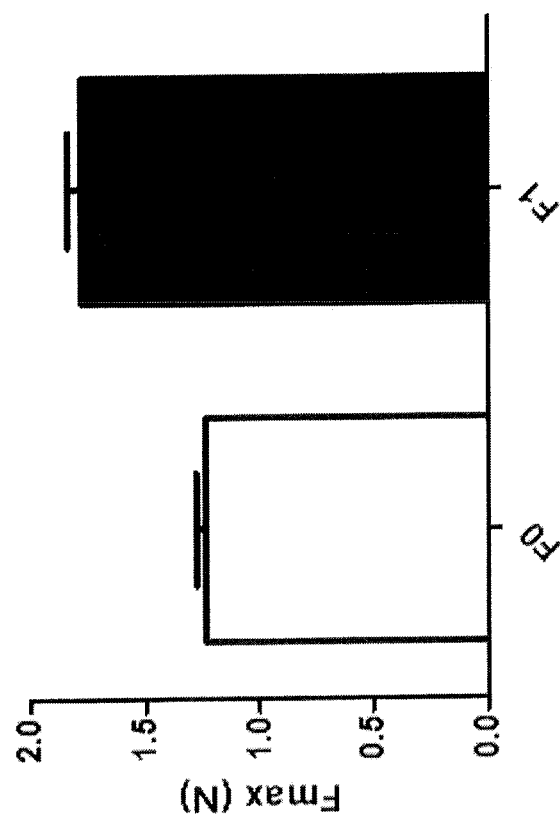
Figure 13:
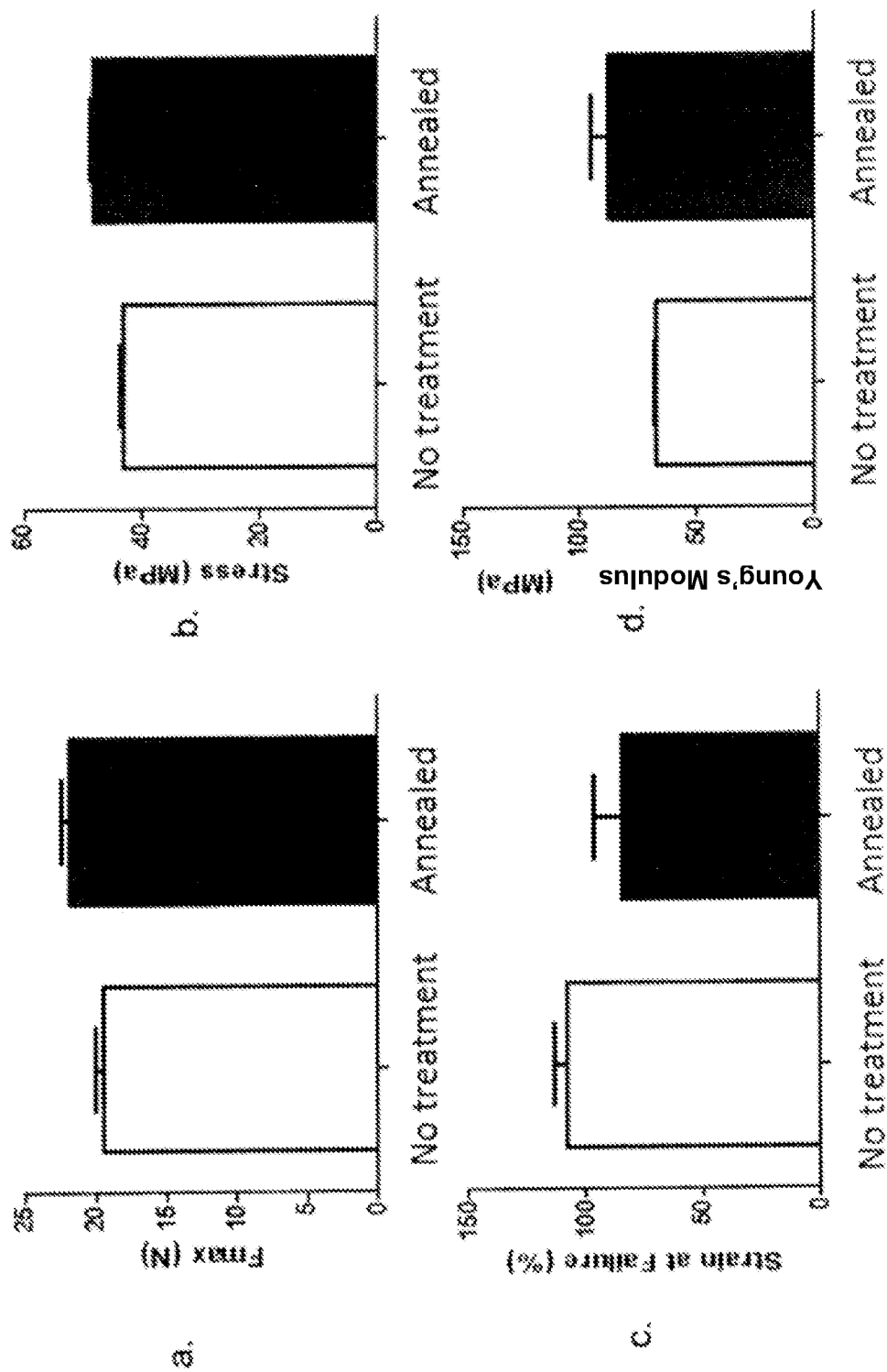
FIGS. 13a to 13d show how annealing treatment can have a significant effect on (a) maximum force, (b) maximum stress, (c) failure strain, and (d) Young's Modulus.

After collection by the wheel 22, the filaments 24 were drawn to prevent material deformation which could occur during further processing and applications. Detached filaments 24 from the apparatus of FIG. 1 were manually stretched up to about 300% of their initial length. In addition to increasing the length of the filament, this also aligned the nanofibres in the direction of the thread, as shown from comparing FIG. 4b (prior to stretching F0) with FIG. 4c (stretched F1). This produces a structure mimetic of native fibrous tissue such as tendon and ligament. Moreover, FIGS. 12a and 12b reveal that while the strain of the filament was dramatically reduced by the treatment, the force at break was significantly improved. According to this example, the stretched filaments were then assembled into a yarn using the method illustrated in FIG. 6. As a final post-manufacture treatment, yarns were annealed for three hours at 65° C. This annealing treatment resulted in a significant increase in strength, stress and Young's Modulus and a decrease in strain, as shown in FIGS. 13a to 13d.

Results:

The degradation profile of the yarns was investigated. It was found that the yarns had completely lost their integrity by week 16. When implanted in a rat model, yarns were still observed 12 weeks after the surgery but no evidence of the material could be found after 20 weeks. The degradation profile suggests that PDO electrospun yarns may be suitable for applications such as tendon repair, since healing of tendon tissue generally occurs within the first three months following surgery.

For biological characterisation, yarns were assembled into a plain weave fabric (FIG. 9) and monofilaments prepared in the same way were used for comparison in vitro. The results suggested that the highly textured surface of the yarn better supported cell adhesion and growth compared to the smooth surface of monofilaments.

The safety of the electrospun yarn was characterised in vivo using a rat model. Observations suggested that the material is safe for implantation and support the idea of a material that will stimulate healing and minimise scar formation.

The invention claimed is:

1. A method for producing a continuous filament from electrospun fibres, comprising:
   passing a conducting wire through free space to provide an elongate, three-dimensional collection surface accessible to electrospun fibres coming into contact with the conducting wire;
   moving the conducting wire in a direction along its length;
   forming an attractive electric field gradient between the conducting wire and a source of electrically charged fibres;
   wherein the conducting wire is moved relative to the source of electrically charged fibres;
   collecting the fibres on the elongate, three-dimensional collection surface of the conducting wire so as to form a continuous filament along the length of the underlying conducting wire;
   wherein the elongate, three-dimensional collection surface of the conducting wire has a three-dimensional shape accessible in free space and the continuous filament thereby being formed with a corresponding three-dimensional shape that corresponds to the three-dimensional shape of the underlying conducting wire; and
   separating the continuous filament from the elongate, three-dimensional collection surface of the underlying conducting wire whilst retaining the corresponding three-dimensional shape of the continuous filament.

2. The method of claim 1, comprising using a blade to separate the continuous filament from the collection surface.

3. The method of claim 1, comprising immersing the continuous filament in a liquid to separate it from the collection surface.

4. The method of claim 1, comprising:
   moving the collection surface with or relative to a non-conducting device spaced radially from the collection surface to interrupt trailing fibres.

5. The method of claim 1, comprising:
   twisting the continuous filament together with one or more other such filaments to produce a yarn.

6. The method of claim 1, comprising:
   providing multiple such collection surfaces in parallel to form multiple filaments; and
   twisting the filaments together to produce a yarn.

7. The method of claim 5, comprising twisting together M filaments in a first direction to form a thread and then twisting together N threads in a second direction opposite to the first direction.

8. The method of claim 1, wherein the fibres have a diameter of at least 1 nm and up to 10 μm.

9. The method of claim 1 comprising braiding the continuous filament together with one or more other such filaments to produce a yarn.

10. The method of claim 5, comprising knitting, weaving or plaiting the yarn with one or more other such yarns into a fabric structure for medical applications, including orthopaedic and soft tissue repair.

* * * * *